United States Patent [19]

Bigham et al.

[11] Patent Number: 5,427,793
[45] Date of Patent: Jun. 27, 1995

[54] TIN-ACRYLATE-CONTAINING POLYMERS AS ALGICIDAL AGENTS IN BUILDING MATERIALS

[75] Inventors: W. Stuart Bigham, Woodbury; Christine A. Sobon, Roseville, both of Minn.; Billy L. George, Hudson, Wis.

[73] Assignee: Minnesota Mining and Manufacturing Company, St. Paul, Minn.

[21] Appl. No.: 50,835

[22] Filed: Apr. 21, 1993

[51] Int. Cl.$^6$ ............................................. A01N 55/04
[52] U.S. Cl. ................................... 424/404; 424/405; 424/408; 424/409
[58] Field of Search .................. 424/78.09, 404, 405, 424/408, 409; 428/144, 147; 427/221

[56] References Cited

U.S. PATENT DOCUMENTS

| | | | |
|---|---|---|---|
| 3,167,473 | 1/1965 | Leebrick et al. | 424/78.09 |
| 3,276,906 | 10/1966 | Nielsen | 117/136 |
| 3,888,683 | 6/1975 | Horai, Jr. et al. | 428/404 X |
| 5,286,544 | 2/1994 | Graham | 428/144 |

FOREIGN PATENT DOCUMENTS

| | | |
|---|---|---|
| 342493 | 5/1989 | European Pat. Off. |
| 0342493 | 11/1989 | European Pat. Off. .... C08F 246/00 |
| 279258 | 5/1990 | Germany . |
| 57-185344 | 11/1982 | Japan .................... 424/78.09 |
| 01-193201 | 8/1989 | Japan . |
| 2084167 | 4/1982 | United Kingdom ............. 124/78.09 |

OTHER PUBLICATIONS

Patent Abstracts of Japan, vol. 013, No. 491 (C-650) Nov. 7, 1989 & JP, A, 01 193 201 (Nitto Kasei Co Ltd), Aug. 3, 1989.
J. Polymer Science, 1958, vol. 32, pp. 523–525.
"Organotin-Based Antifouling Systems", Chapter 2.

*Primary Examiner*—Thurman K. Page
*Assistant Examiner*—Peter F. Kulkosky
*Attorney, Agent, or Firm*—Gary L. Griswold; Walter N. Kirn; Ramon R. Hoch

[57] ABSTRACT

Granular materials having a tin-acrylate polymer coating are described which are algae-resistant. A method of inhibiting the growth of algae on roofing granules and other particulate materials attached to substrates by the use of tin-acrylate-containing polymers either as a topical treatment or as a polymeric binder is also presented. The methods presented are an advancement in the art in that in addition to algae-resistance, the polymers also confer other desirable properties to the granules onto which they are coated, such as increased adhesion to asphalt shingles.

13 Claims, No Drawings

TIN-ACRYLATE-CONTAINING POLYMERS AS ALGICIDAL AGENTS IN BUILDING MATERIALS

BACKGROUND OF THE INVENTION

1. Field of the Invention

The present invention relates to acrylic polymers containing pendant tin moieties and their use in the long-term inhibition of algae growth on building materials such as conventional asphalt shingles.

2. Description of Related Art

Pigmented granules, both natural and artificially color-coated, find extremely wide use in roofing and siding materials, such as in granule-surfaced bituminous roll roofing and asphalt shingles. The granules, which are partially imbedded in one surface of asphalt-impregnated and/or asphalt-coated fiber sheet material, form a coating to provide an inherently weather-resistant, fire-resistant, and decorative exterior surface. It is also preferred that the roofing granules provide resistance to ultraviolet radiation degradation.

Roofing granules generally consist of crushed and screened inorganic substrate granules which may have their own inherent color. The substrate granules are typically coated with a ceramic coating which may include a pigment.

The useful life of roofing shingles depends upon permanent coverage of the shingle backing by roofing granules. It is thus important that roofing granules be firmly embedded in the adhesive (asphalt in the case of asphalt shingles).

Discoloration of roofing shingles and other building materials due to algae infestation has become especially problematic in recent years. Though the phenomena has traditionally been observed in the south and northwest portions of the United States, its presence has been observed in most areas of the country. Typically, the discoloration is found on the northern slope of a roof where moisture is retained. The infestation may be particularly acute on asphalt shingles. Discolorization has been attributed to the presence of a blue-green algae, *Gloeocapsa magma*, transported through air-borne particles. The increased usage of calcium carbonate as an asphalt filler in the asphalt shingle manufacturing process is partially responsible for sustained algal growth. Calcium is a macronutrient for *Gloeocapsa magma*, thus the use of limestone filler provides an unlimited food supply in which the algae can feed. In addition, *Gloeocapsa magma* is a fairly robust strain of algae which is able to tolerate a variety of climates due to the desiccation properties of the gelatinous sheath surrounding the algae cells.

So-called "tin-acrylate" monomers and polymers were described by Montermoso (*J. Polymer Science*, 1958, volume 32, pages 523–525). Montermoso describes the synthesis of the trialkyltin ester of methacrylic acid and polymerization of this monomer to form a tin-acrylate polymer.

One of the most extensive uses of this type of polymer has been in antifouling paints such as used to paint ship hulls and the like. Polymers of this type have also been applied to fish nets to provide fouling control, and as protective coatings for wood, latex paints, and plaster. Various polymers, co-polymers, and terpolymers having a plurality of covalently bonded organotin complexes thereon have been described in trade literature. See for example German Democratic Republic Patent Publication No. DD 279258 A1, published May 30, 1990; Japanese Patent Kokai 01193201 A2, published Aug. 3, 1989; and European Patent Application No. EP 342493 A2, published Nov. 23, 1989.

All of the known uses of tin-acrylate polymers are either in alkaline environments such as sea water, or the substrate to which the tin-acrylate polymer is applied is an uncomplicated substrate where there is no problem of adhesion of a granular material to the substrate, such as in the case of roofing granules adhered to asphalt shingles. The inventors herein are not aware of any use of tin-acrylate polymers in an environment where a granular material is to be adhered to a substrate surface which might sustain growth of algae.

SUMMARY OF THE INVENTION

In accordance with the present invention, a method of inhibiting the growth of algae on building materials by the use of tin-acrylate-containing polymers is presented. As used herein "tin-acrylate polymer" means a polymer that contains at least one pendant alkyl-tin moiety. "Alkyl-tin moiety" includes monoalkylated, dialkylated, and trialkylated tin moieties. When the polymers are applied to roofing granules, the polymers may be applied either as a topical treatment on a shingle or as a binder in lieu of ceramic binders.

This method represents an advancement in the roofing granule art in that in addition to algae-resistance, these polymers also confer other desirable properties to the granules to which they are coated. In particular, the tin-acrylate-coated granules exhibit excellent adhesion to asphalt typically used in asphalt shingles, are resistant to staining from the asphalt, and, when applied during processing of the granules, reduced dust generation from the granules. However, the method is also applicable to other building materials, particularly those including calcium, such as shells, concrete, and stucco.

One aspect of the present invention is an algicidal granular material having an algicidal coating on base granules, the coating comprising an organic oil and a tin-acrylate polymer dispersed therein. The tin-acrylate polymer is derived from a monomer composition comprising free-radical polymerizable units independently selected from the group consisting of:

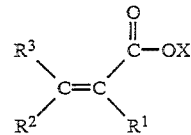

I wherein:

X is selected from the group consisting of $SnR^4R^5R^6$ and hydrogen;

$R^1$–$R^3$ inclusive are the same or different and independently selected from the group consisting of hydrogen and organic radicals having from 1 to about 20 carbon atoms; and $R^4$–$R^6$ inclusive are the same or different and independently selected from the group consisting of hydrogen and alkyl groups having from 1 to about 7 carbon atoms;

with the provisos that $R^1$–$R^6$ inclusive are selected so that the polymer has a weight average molecular weight ranging from about 5,000 to about 50,000 (more preferably from about 5,000 to about 15,000) and the polymer has an effective amount of $SnR^4R^5R^6$ groups to render the granular material algicidal.

The preferred organic oil for use in this aspect of the invention is a hydrotreated (i.e., desulfurized) mineral oil selected from the group consisting of slate oil, rock oil, coal oil, and seneca oil. The preferred mineral oil is slate oil.

As used herein the term "algicidal" when referring to a granule or a composite sheet body means that the granule or composite has an amount of a tin-acrylate polymer sufficient to kill or substantially prevent growth of algae, preferably the blue-green algae *Gloeocapsa magma*.

"Algicidal coating" means a coating comprising a tin-acrylate polymer dispersed within an organic oil, which preferably covers the entire surface of the granule.

The term "algicidal polymeric binder coating" means an acrylic polymer coating (including copolymers, terpolymers, and the like) having an effective amount of $SnR^4R^5R^6$ moieties, derived from polymerizable units within general formula I, which at least partically coats the granule surface.

The term "algicidal topical coating" means a coating comprising polymerized or unpolymerized units within general formula I which is brushed onto a surface which is either to be protected from algae infestation or to kill existing algae. If unpolymerized units are employed, exposure to an energy source is required to achieve the desired degree of polymerization which the user desires. This in turn depends on the length of time the user desires the algicidal effect to be present.

A second aspect of the invention is an algae-resistant granular material having a polymeric binder coating on base granules, the polymeric binder coating comprising the tin-acrylate polymers described in the first aspect of the invention. In this aspect of the invention, the tin-acrylate polymer forms an organic binder to replace or coat over the conventional ceramic binder typically coated onto base granules. A monomer composition comprising monomers within general formula I above is applied to a base granule and the coated granule exposed to conditions sufficient to polymerize the monomers, thus forming a tin-acrylate polymeric coating. The tin-acrylate polymeric binder coating may be pigmented or nonpigmented.

A third aspect of the invention is an algicidal composite sheet body suitable for use as building material comprising a bituminous sheet material having a firmly adherent surfacing of granular material, at least some of the granular material being algae-resistant granules of the first and/or second aspects of the invention.

A fourth aspect of the invention is an algicidal composite sheet body suitable for use as roofing and siding material. The composite comprises a bituminous sheet material having a firmly adherent surfacing of granules, the granules adhered to the bituminous sheet material by an asphalt composition. The granules and asphalt form an exterior surface on the composite sheet body. The composite sheet body exterior surface has a topical coating thereon comprising the coating described in the first aspect of the invention.

A final aspect of the invention is a method of use of tin-acrylate polymers to eliminate existing algae or control the growth of new algae on particulate matter building materials, especially where there is a source of calcium present. In its broadest embodiment the method comprises first applying to particulate matter a composition comprising the tin-acrylate polymer described in the first aspect of the invention to form coated particulate matter. The second step comprises allowing the composition to remain on said particulate matter for a period of time sufficient to prevent growth of algae or eliminate (i.e. kill) existing algae.

One preferred embodiment of the method of the invention comprises applying a tin-acrylate polymer/organic oil mixture as a topical coating to the surface to be treated. Another preferred embodiment of the method of the invention comprises applying a tin-acrylate polymer/organic oil composition to particulate matter such as roofing granules, and adhering the granules to the surface to be protected. A third preferred embodiment of the method of the invention comprises applying to particulate matter a monomer composition comprising monomers within general formula I, exposing the monomers to conditions sufficient to polymerize the monomer, and applying the particulate material to a surface. In these method, it is of course a proviso that an effective amount of monomers within general formula I have algicidal property.

Particulate matter such as roofing granules treated as described in accordance with the invention exhibit excellent alkalinity, water repellency, adhesion to asphalt, and stain resistance as measured in accordance with standard test procedures.

Further aspects and advantages of the invention will become apparent upon reading the description of preferred embodiments and examples which follow.

Description of Preferred Embodiments

I. Tin-Acrylate Monomers and Polymers

Tin-acrylate monomers useful in the invention have a general structure:

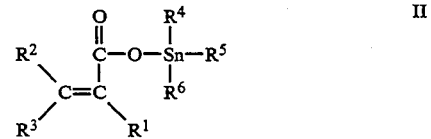

wherein $R^1$–$R^6$ inclusive are defined as mentioned previously. Preferably, $R^4$ $R^5$ and $R^6$ are the same linear alkyl groups, such as n-butyl. The production of this monomer, which is a trialkyltin ester of methacrylic acid, may be synthesized by the method of Montermoso (*Journal of Polymer Science* 1958, 32, 523–525) which is incorporated herein by reference, and further described in Example 1 below.

Tin-acrylate polymers useful in the invention may be produced by dissolving monomers within general formula I (with an effective proportion of these monomers being within general formula II) and a small amount of a free radical initiator such as benzoyl peroxide in a suitable inert solvent such as benzene, essentially following the method of Montermoso, previously incorporated herein by reference. The molecular weight of the resulting polymer may be increased in an indirect relation to the amount of oxygen present during the polymerization. In other words, if high molecular weights are desired, oxygen should be substantially eliminated from the reaction. After the solvent has been removed (such as by vacuum distillation) the desired tin-acrylate polymer is obtained typically as a clear, pale yellow, rubbery solid which is insoluble in benzene, water, chlorinated solvents, and aqueous acids, such as aqueous hydrogen sulfate.

Once the tin-acrylate polymer has been formed, the polymer may be applied to building materials by first melting the polymer and thereafter adding an appropriate amount of an organic oil, which functions as a carrier for the polymer. The polymer/oil mixture may then be applied to particulate or granular materials by placing heated granular material in a shaking device and adding the polymer/oil mixture thereto.

Alternatively, if the polymer/oil mixture is to be applied to a surface, such as a stucco wall or to a calcium-containing surface such as marble, the polymer/oil mixture may be applied as a topical coating with a weight percentage of polymer ranging from about 0.5 to about 15 weight percent. When the tin-acrylate polymer is mixed with the organic oil and used as a post-treatment on granular materials such as kiln-fired ceramic-coated base granules, typically from about 0.2 grams to about 5 grams of polymer/oil mixture is applied to 1 kilogram of base granules, with the weight percent polymer ranging from about 50 to about 90 weight percent as a percentage of polymer and oil, more preferably ranging from about 75 to about 90 percent. When less than about 50 weight percent polymer is used, the water repellency of the roofing granules may decrease considerably, dropping to about 0 seconds (see Water Repellency Test in the test methods) when less than about 10 weight percent polymer is used, which is undesirable.

When monomers within general formula I above are used to form polymeric binder coatings for particulate material such as roofing granules, the monomers and a free radical initiator, such as benzoyl peroxide, are combined along with a suitable solvent such as benzene in a container. In a separate container, a surfactant composition is formed typically and preferably comprising distilled water and a surfactant, preferably a fluorochemical surfactant. In a third container, raw base granules may be combined with a pigment, such as titanium dioxide, and a clay such as kaolin clay as a secondary pigment. The raw base granules and pigment are dry mixed until the pigment is well dispersed onto the base granule surface. Then small amounts of the surfactant composition and the monomer/initiator combination are added to the pigmented base granule container until all of the base granules are uniformly coated. The coated base granules are then exposed to conditions sufficient to initiate polymerization of the monomers. Preferably, this is accomplished by thermally inducing the polymerization in an oven, however other methods such as ultraviolet radiation, visible radiation, and electron beam irradiation may be used.

It is considered within the scope of the invention to coat building materials such as particulate materials with a copolymeric or terpolymeric binder coating by using two or more monomers within general formula I. A typical and preferred terpolymer is described in German Democratic Republic Patent Publication No. DD 279258 A1, published May 30, 1990, comprised of a 58:39:3 mole ratio of methylmethacrylate:tributyltinacrylate:polyethylene glycol monoacrylate. Japanese Patent Kokai 01193201 A2, published Aug. 3, 1989, describes a useful copolymer of tributyltinmethacrylate and methylmethacrylate. European Patent Application No. EP 342493 A2, published Nov. 23, 1989, describes a polymer useful in the invention based on reacting the following monomers: methylmethacrylate, butylacrylate, tributyltinmethacrylate, acrylic acid, and acrylamide.

One particularly preferred class of copolymers for use in the invention are copolymers of trialkyltinacrylates with methacryloxyalkyltrialkyloxysilanes. In these embodiments, in the container containing the monomers is included a siloxyl-acrylate monomer, preferably in a 1:1 molar ratio based on moles of monomers within general formula II. The particular copolymer of tributyltinmethacrylate with methacryloxypropyltrimethoxysilane, when used as polymeric binder for roofing granules produced a significantly improved value for the adhesion and alkalinity tests, as may be seen by comparing Examples 11 and 12 herein.

II. Base Granules

Inorganic substrate granules useful in the invention are conventional and may be selected from any one of a rather wide class of relatively porous and weather-resistant rocks, minerals, or recycled materials. Examples of relatively porous materials are trap rocks and slates. Examples of relatively non-porous rocks or minerals are argillite or greystone (such as the large greystone deposits located north of Wausau, Wisconsin), greenstone, certain granites and the like. Normally, it is preferred to employ the relatively non-porous rocks, although even these rocks have a substantial porosity as compared to the ceramic coating on the inorganic substrates.

III. Ceramic-Coated Base Granules

For production of ceramic-coated base granules, the ceramic coating generally comprises the reaction product of an aqueous alkali metal silicate with an aluminosilicate clay, which react in the presence of heat to form a hard ceramic coating. Although the term "coating" is used herein, and although the ceramic reaction product preferably completely covers the base granule, this is not required.

Aqueous sodium silicate is the preferred alkali metal silicate due to its availability and economy, although equivalent materials such as potassium silicate may also be substituted wholly or partially therefore. The alkali metal silicate may be designated as $M_2O:SiO_2$, where M represents an alkali metal such as sodium (Na), potassium (K), mixture of sodium and potassium, and the like. The weight ratio of $SiO_2$ to $M_2O$ preferably ranges from about 1.4:1 to about 3.75:1. Ratios of 2.75:1 and 3.22:1 are particularly preferred, depending on the color of the granular material to be produced, the former preferred when light colored granules are produced, while the latter is preferred when dark colored granules are desired.

Aluminosilicates for use in the ceramic coatings are preferably selected from clays having the formula $Al_2Si_2O_5(OH)_4$. Another preferred aluminosilicate is kaolin, $Al_2O_3 \cdot 2SiO_2 \cdot 2H_2O$, and its derivatives formed either by weathering (kaolinite), by moderate heating (dickite), or by hypogene processes (nakrite). The particle size of the clay is not critical to the invention; however, it is preferred that the clay contain not more than about 0.5 percent coarse particles (particles greater than about 0.002 millimeters in diameter). Other commercially available and useful aluminosilicate clays for use in the ceramic coating of the granules in the present invention are the aluminosilicates known under the trade designations "Dover", from W. R. Grace Chemical Company, Mcintyre, Ga. and "Sno-brite" from Evans Clay Company, Mcintyre, Ga.

Pigments useful in the invention include carbon black, titanium dioxide, chromium oxide, yellow iron oxide, phthalocyanine green and blue, ultramarine blue, red iron oxide, metal ferrites, and mixtures thereof. One preferred pigmented algicidal granule is a black granule wherein the pigment consists essentially of a mixture of two carbon blacks and chromium oxide, the first carbon black having an average particle size ranging from about 50 to 100 nanometers, more preferably from 70 to 80 nanometers, and the second having an average particle size ranging from about 15 to 50 nanometers, more preferably from about 20 to 30 nanometers. In these black granules the total amount of carbon black preferably ranges from about 1.0 to 2.0 grams per kilogram substrate granules, with the weight ratio of larger particle size to smaller particle size carbon black ranging from about 3.0 to 5.0. The amount of chromium oxide may range from about 1.25 to about 1.75 grams per kilogram substrate granules. One carbon black having a particle size of 25 nanometers is known under the trade designation "Black Pearls 130". A carbon black having a particle of 75 nanometers is known under the trade designation "Black Pearls 490".

A dispersant is typically and preferably used to disperse the carbon black or other fine particle size pigments used in the invention. One such dispersant is the sodium salt of sulfonated naphthalene-formaldehyde condensate known under the trade designation "Blancol N", available from Rhone-Poulenc Surfactants & Specialties, Cranbury, N.J. The dispersant is typically used in an amount ranging from about 0.01 to about 1.0 gram per kilogram of substrate granules. When a mixture of two or more carbon blacks is used, as described above, the amount of dispersant more preferably ranges from about 0.03 to about 0.1 gram per kilogram substrate granules.

IV. Building Materials Which May Be Protected From Algae Infestation

Two general categories of building materials may be protected from algae infestation using the tin-acrylate polymers described herein. The first general classification is calcium-containing materials such as calcium carbonate-containing structures, such as bridge overpasses, stucco siding on commercial and residential buildings, and the like. In this type of building material, the tin-acrylate polymer is normally applied as a mixture of tin-acrylate polymer and organic oil as herein described. Any type of material may be used to spread the tin-acrylate polymer/organic oil composition onto the surface to be protected, examples including a paintbrush, a nonwoven pad, and the like. It may be possible to use a spray device for application if a monomer composition is applied to the surface, with exposure to an energy source subsequent to the application step. If the surface to be protected is exposed to sunlight during application of a composition containing tin-acrylate polymer, a single coating is all that is usually required, the tin-acrylate polymer being water repellent and not easily washed off.

The second general category of building materials to be protected using tin-acrylate polymers described herein are particulate building materials such as roofing granules as described hereinabove. However, the invention is not to be limited to the application of the tin-acrylate polymers to roofing granules, since the polymers may be applied to, for example, rocks which are typically found in flower beds, and the like. Also, the base granule may not itself be calcium-containing but may be applied to a surface or in an environment exposed to calcium ion, such as the case when roofing granules are adhered to calcium carbonate-filled asphalt. Calcium carbonate is typically used as a filler in asphalt to extend the asphalt and produce a less expensive shingle.

The invention will be further understood with reference to the following test methods and examples, in which all parts and percentages are by weight unless otherwise specified.

Test Methods

Accelerated Algae Growth Panel Test

In order to determine the effects of the tin-acrylate polymers on preventing algae growth on otherwise conventional asphalt shingles, shingles incorporating the principles of the invention were exposed to the environment in Houston, Tex.

In each test, a commercially available new asphalt shingle was nailed to a 61 cm×76.2 cm north-facing masonite particle board panel which was at an angle to horizontal of 45°. Each shingle had a drip edge on the bottom and a 2.54 cm wide aluminum strip attached to the top, and the nails passed through the aluminum strip on the top. If a tin-acrylate/oil topical coating was used, the coating was applied by a brush.

Shingles were monitored every 6 months for algae growth by making a visual review of the shingles and rating the shingles 1 to 5, where 1 is no algae and 5 is complete algae infestation.

Alkalinity Test

This test provided a measure of the unbound, soluble alkali metal content remaining in a ceramic coating made from reacting an alkali metal silicate and an aluminosilicate clay. The silicate binder reacts (when calcined at temperatures preferably at about 500° C.) with an aluminosilicate clay, and the reaction product forms a water insoluble ceramic coating. The remaining soluble alkali metal (mostly typically in the form of NaCl or other alkali metal chloride) is an indirect measure of the extent of insolubilization of the ceramic coating.

5-minute Alkalinity Test

For each test run, 100 milliliters (ml) of boiling water was poured into an Erlenmeyer flask (which had previously been boiled free of soluble alkali). 25 grams of granules to be tested were added to the boiling water as were 3 drops of phenolphthalein indicator (turning point pH=9, where "pH" is defined as the negative base ten logarithm of the hydrogen ion concentration). The water, granules and indicator were boiled for a period of 5 minutes. Decantation of the boiling water was performed into an Erlenmeyer flask. Approximately 10 ml of fresh cold distilled water was then added onto the boiled granules and swirled. The water was then added to the original boiled water that had already been decanted.

The total amount of water was then titrated to endpoint using a digital buret titration device commercially available from the Brinkmann Company. If the solution was pink immediately after addition of the indicator, that indicated the solution had a pH above 9.0, so the solution was titrated with acid, (sulfuric acid (0.1N)). If the solution was not pink immediately after addition of the indicator, the solution had a pH less than 9.0, and thus needed to be titrated to end-point using a base, (0.1N sodium hydroxide).

The ml of acid or base required to reach end-point is called the "alkalinity". The alkalinity is positive when using acid, negative when using base. To clarify this procedure, the following theoretical examples are offered:

Theoretical Example 1

100 grams of granular materials are prepared as above. The decanted solution is pink, and 1.4 ml of sulfuric acid is added to the solution to reach end-point (end-point is reached when the phenolphthalein indicator turns color from pink to clear). The alkalinity for this example would be +1.4.

Theoretical Example 2

100 grams of granular materials are prepared as above. The decanted solution is clear, and requires 0.5 ml of sodium hydroxide to make the solution turn pink, thereby indicating end-point. The alkalinity of this example would be −0.50.

For granular materials of the invention, any alkalinity result between −2.0 and +2.0 is acceptable. In general, alkalinity values that are less than 0.2 units apart are considered to be essentially the same value.

15-minute Alkalinity Test

This test was identical to the 5-minute Alkalinity Test except that the water, granules, and indicator were boiled for exactly 15 minutes.

21-hour Alkalinity Test

External factors which might cause granules to become highly alkaline can result in poor adhesion. For example, when a shingle manufacturer packages shingles hot and wet and the heat is retained in a bundle of shingles, granules that are not properly neutralized can revert to the alkaline state. Thus, a granule that has an alkalinity of +2.0 (at the time of manufacturing) might develop an alkalinity of +8.0 after heating to 52° C. and high humidity. Thus, a granule which retains its 5-minute alkalinity is preferred.

The procedure for 21-hour alkalinity was similar to the 5- and 15-minute Alkalinity Tests, except that after the granules were added to the distilled water, the flask stoppered and then placed in an oven maintained at 49° C. for 21 hours. After 21 hours, the solution in each case was decanted into a clean 250 ml Erlenmeyer flask and the granules rinsed once with 10 ml of cold distilled water. The rinse water was added to the decanted solution, 3 drops of phenolphthalein added, and the solutions titrated as in the 5- and 15-minute alkalinity tests.

Water Repellency Test

This test was used to indicate whether a coating applied to a base granule had been uniformly spread thereon immediately after the coating has been applied.

25 grams of full grade granules having the coating to be tested thereon were poured into a conical pile. The apex of the pile was then depressed with a round end of a test tube. Three drops of distilled water were then placed in the depression using an eye dropper while simultaneously starting a stop watch. The time required for the bead of water to break up and sink down through the granules was recorded as the value of the water repellency test. The higher the value, the more uniform the spread of the applied coating.

Reverse Wettability Test

This test was used to determine the completeness of distribution of tin-acrylate polymeric binders applied to roofing granules by trying to adhere asphalt to the granules while stirring in water.

First, an asphalt was prepared that was soft enough to pour readily at about 15° C. by adding 13 parts of a Mid-Continent 54.5° C. melt point saturant to 10 parts by weight of 635 oil. The mixture was then heated with stirring at a temperature not exceeding about 120° C. until the asphalt became thoroughly dissolved in the oil. The mixture was allowed to cool before using.

To an estimated quantity of 10 grams of granules in a 100 milliliter ("ml") beaker was added about 50 ml of water. With a suitable spatula about 2 grams of asphalt was placed into the granules-water mixture and stirred for one minute, constantly attempting to coat the granules with asphalt. While the whole mass of granules and asphalt was under water and after cessation of stirring, the percentage of total granule surface coated by the asphalt was then estimated. Also estimated was the percentage of loose granules lying in the bottom of the beaker which are entirely uncoated with asphalt. Both percentages are reported. For example, if the percent of total granule surface covered (including loose granules) was 75% and the percent of loose granules in the bottom of the beaker was 4%, the figures reported were 75-4.

At the end of five minutes, the mass was observed again and the percentages estimated again. Reported are the lower of the two sets of figures. Well-treated granules lie in the range of 90–100 percent with no loose granules.

Adhesion Tests (Dry and Wet Rub Tests)

The rub test was used to predict the adhesive characteristics of roofing granules toward asphalt. The weight loss of an asphalt shingle due to granule loss after being rubbed was compared with the original weight of the shingle. If the weight loss is less than 0.1–0.3 gram the shingle is considered to pass the test.

Effects of water upon adhesion were obtained by submerging the asphalt shingle to be tested in distilled water at room temperature (about 20° C.) for 1 and 7 days. Afterwards, observation of the weight loss from the shingles was determined as in the dry rub test (after the wet shingles were towel dried and then air-dried for 1–2 minutes. Weight loss values of 1 gram or less are considered satisfactory.

I. Preparation of Granules

Full grade granules were screened through a #14 screen (US mesh) (average particle size of 1.4 micrometers) and those granules which remained on the screen were used to prepare asphalt shingles used in the rub test.

II. Preparation of Asphalt Shingles

A coating asphalt obtained from a typical mid-continent (US) crude oil was used as obtained from Richards Asphalt Co., Savage, Minn. The asphalt was heated to about 227° C. in a table-top shingle maker, while sufficient calcium carbonate was added as filler so that the weight percent calcium carbonate per total weight of asphalt was 65 weight percent. Experimental strips (5.1 cm × 22.9 cm) of asphalt shingles were made using the table-top shingle maker by extruding the calcium carbonate-filled asphalt onto organic backing materials at 227° C.

The dry rub test is performed by first weighing the test shingle in each case to obtain an original weight A (grams), then clamping the ends of the test shingle into a horizontal holder so that a bristle brush moving across the granule surface in a reciprocating fashion was able to abrade the granule surface. In each rub test the brush was reciprocated across the shingle so that 50 cycles were completed (50 forward, 50 back strokes). After abrasion, the test shingle was removed and tapped gently to remove loose granules, then reweighed to obtain weight B (grams). The rub test result is reported as A-B (grams).

L*a*b* Scan Colorimetric Determinations

Since color is the first stimulus that the consumer perceives, resulting in an immediate evaluation of roofing granule quality, color consistency is one of the principal quality attributes of roofing granules. To determine the color of algicidal roofing granules within the invention, a machine known under the trade designation "HunterLab LabScan Spectrocolorimeter" model 6000 was used. A sample preparation device, which is described in U.S. Pat. No. 4,582,425, was used to prepare the samples.

The spectrocolorimeter is designed to measure the reflectance color of objects. The spectrocolorimeter measuring geometry used was 0°/45°. This geometry provided for viewing the samples similar to normal visual evaluation, with 0° illumination, or perpendicular illumination of the sample, in 45° viewing of the sample. 45° circumferential viewing effectively excludes the specular (glossy) reflectance. This geometry essentially eliminated the effect of the sample directionality or granule texture.

As explained in the HunterLab LabScan Spectrocolorimeter brochure, light from a halogen lamp passes through a series of filters and lenses to simulate D65 daylight and eliminate heat, and is focused on the sample in a circular pattern. (Roofing granular color was read in "Illuminant D65" which represents daylight with a correlated color temperature of approximately 6500° Kelvin.) Light diffusely reflected from the sample is collected by sixteen fiber optic bundles staged circumferentially at 45° to the sample. The light input from all stations was averaged to eliminate errors caused by sample texture and directionality, and was then directed onto the circular variable filter which was spun continuously, separating the light into its component wavelengths. The separated light was picked up by a single photo detector, and then fed to a personal computer via an analog-to-digital converter. The computer processes measurement data at 10 nanometer intervals across the visual spectrum, from 400 to 700 nanometers.

For the color determination tests, the 10° CIE Standard Observer (CIE stands for the Commission Internationale de l'Eclairage, an international commission on illumination). The "Standard Observer" is the spectral response characteristic of the average observer defined by the CIE. Two such sets of data are defined, the 1931 data for the 2° visual field (distance viewing) and the 1964 data for the annular 10° visual field (approximately arms length viewing). A much better agreement with the average visual assessment can be obtained by making use of the 10° standard observer, and thus this was the observer used in these tests.

For each color granule tested, a sample was scanned by the spectrocolorimeter. This scan produced a numerical description of the colored sample, a fingerprint, which never changes. However, since it does not consider the lighting condition and the observer, the CIE L*a*b* does not completely describe the visual appearance of the color. A mathematical means of translating fingerprints into a set of three numbers (XYZ), tristimulus values, was developed. The tristimulus values describe color as a normal observer sees it under a specific lighting condition.

Because the tristimulus values (XYZ) do not provide either uniform or logical estimates of perceived color intervals or color relationships, scales based on the CIE standard observer were transformed into the "opponent-colors" theory of color vision. The 1976 CIE L*a*b* is one such transformation. The opponent-colors theory maintains that the interaction between the eye and the brain decodes the experience of a color into three specific signals. One of these signals is lightness-darkness (L*), one is red-green (a,) and one is yellow-blue (b,). This color system was chosen for use in these tests because it is believed to be understandable by both the color scientist and the novice. Thus all instrument color readings were taken on a HunterLab LabScan Spectrocolorimeter, in Illuminant D65, with 10° observer, in 1976 CIE L*a*b* color space. All granular samples were red after an oil had been removed from the granules. The oil removal procedure is described in the following test procedure.

After the granules were deoiled, the granule preparation procedure of U.S. Pat. No. 4,582,425 was used. Briefly, this procedure consisted of loading a layout sample dish by slightly overfilling the dish with granules, compressing the granules into the dish with the flat surface of a layout tray, using only vertical pressure and no circular action. The loaded sample dish in each test was positioned on the layout device, matching the configuration, so that the sample dishes were in the locked position. A roll carriage was then gently lowered onto the sample dish, after which the roller is pulled back and forth across the surface on the face of the granules. It was found that twice across the surface produced the desired smooth, even, flat, and undented surface necessary for precise color readings. Excess granules fall over the sample dish edge.

The prepared granule sample dish was then placed into the instrument sample port. The sample surface was first examined to insure that the sample has not "popped" and lost its smooth level surface.

Two complete spectrocolorimeter readings (scans) were taken, completely emptying and repeating the layout procedure each time. The procedure was repeated until two readings consistent with each other to within less than 0.3 unit range were obtained. If not, the procedures were repeated with more attention to detail. All samples presented to the spectrocolorimeter for color difference determination were at ambient temperature (hot granules give inaccurate color readings, as well as wet granules). After deoiling the granules in accordance with the procedure explained below, the granules were in all cases read within four hours of deoiling. (Samples left in an uncontrolled condition may exhibit unwanted changes, and samples that have been deoiled and then left standing for a long period of time are not acceptable for spectrocolorimeter readings.)

In interpreting the results from the spectrocolorimeter, the opponent-color scales give measurements of color in units of approximate visual uniformity throughout the color solid. $L^*$ measures lightness and varies from 100 for perfect white, to zero for black, approximately as the eye would evaluate it. $a^*$ and $b^*$, the chromaticity dimensions, give understandable designations of color as follows: $a^*$ measures redness when plus, grey when zero, and greenest when minus; and $b^*$ measures yellowness when plus, grey when zero, and blueness when minus. Acceptable opponent color scales for the algicidal granules of the present invention are when all three of $L^*$, $a^*$ and $b^*$ are within $+/- 1.0$ of the standard non-algicidal black roofing granules, more preferably within $+/- 0.5$ of the $L^*$, $a^*$ and $b^*$ measures of the non-algicidal roofing granules.

Deoiling Procedure

As explained previously, oil is frequently added to roofing granules as an adhesion medium between the asphalt and granule as well as for reducing dust generation during processing of the granules. For quality control, exposed color is the most critical feature; therefore, the exposed color must be assimilated through the deoiling process. The deoiling procedure uses the following equipment:
deoiling funnel,
1,1,1-trichloroethane,
100 milliliter beakers,
distilled water,
vent hood,
vented oven,
screens (Tyler 14 and 20),
timer,
screen brush,
one gallon can,
stirring rod, and
white paper towels.

A sample of oiled granules was first screened to mesh size $-14/+20$. The screened sample was then placed in a 100 milliliter beaker, the granules filling up to 50 milliliters of a beaker. The beaker was then filled to the rim with 1,1,1-trichloroethane. The granules and trichloroethane were then allowed to sit undisturbed for about five minutes. The granules and trichloroethane were then poured into a deoiling funnel and the solvent drained without stirring into a one gallon can. Next, the funnel was filled with distilled water to the rim and stirred while draining, being sure to collect all solvent and water for proper disposal. The remaining granule samples in the funnel were placed on a white paper towel and dried in a vented oven. The temperature of the oven depended on how long the result can be waited for. At temperatures ranging from about 80° C. to about 110° C., the samples merely needed to be taken out when dry. (At temperatures above 110° C., the samples must be closely watched and removed as soon as possible when dry or the color can be affected. Too long a drying time at a temperature below about 80° C. can result in some "blooming" which will also affect spectrocolorimeter results.) The temperature of the drying oven used for these examples was 150° C. Finally, the dried granules were cooled on paper towels to room temperature on a table top prior to making any color determinations.

4-Day Stain Test

Some roofing granules, when placed on asphalt shingles, have the property of absorbing oils from the asphalt after extended storage, resulting in darkening and yellowing of the shingle color. The color change is commonly referred to as "staining." As measured using the above-referenced colorimetric test, staining for white pigmented granules is defined as the sum of the absolute value of the darkening (a negative $L^*$) and yellowing (a positive $b^*$) of a 4-day stain panel versus its original 0-day stain panel counterpart.

Roofing granules, asphalt, and storage conditions of the shingle are factors in staining. This test was used to evaluate the staining caused by the granules alone by holding the asphalt and storage conditions constant.

Asphalt fiberglass spreads were previously prepared using a pilot scale shingle maker. A 4-day staining oven was preheated to 80° C., and a panel preparation oven (including trays) was preheated to 188° C. Meanwhile, a number of 10.2 centimeter ("cm") ×30.5 cm stain panels were cut from the asphalt fiberglass spreads.

To prepare a granule-coated stain panel, the panel preparation oven was reduced in temperature to 182° C. and a stain panel was placed on a tray in the oven for 3 to 4 minutes to melt the asphalt sufficiently so that granules could be applied thereto. (The asphalt was sufficiently heated when it just ran off the fiberglass spread and had a glossy, shiny appearance.)

A granule delivery jar was filled with about 125 grams of granules. The jar was then covered with a lid having a predetermined number and spacing of holes so that an even distribution of granules was obtained on the granule-coated stain panel. For grade 11 granules, 0.64 cm diameter holes were used.

Silicone release agent was applied to a stainless steel tray and spatulas used to transfer the stain panels from the panel preparation oven. A stain panel was removed from the panel preparation oven with a spatula and placed on the stainless steel tray. Immediately (in no more than 8 seconds) thereafter a quantity of granules sufficient to just cover the stain panel were applied using the delivery jar. The stainless steel tray was then tipped a lightly shaken to remove excess granules. The granules still sticking to the asphalt were then quickly embedded into the asphalt with the bottom of a 250 ml Erlenmeyer flask, being careful not to dig the granules into the soft asphalt. Immediately thereafter, a second quantity of granules were applied, the tray tipped and shaken, and the granules embedded, with the object being not to have every space of asphalt covered but to ensure that the granules were well embedded and surrounded with asphalt.

The granule-coated stain panel was then placed on a flat surface to cool to room temperature (about 25° C.). From the cooled panel, two pieces were prepared by cutting with a paper cutter: a 7.6 cm×10.2 cm panel which was used as the 0-day stain panel, and the remaining 10.2 cm×22.9 cm panel, which was used as the 4-day stain panel. The 0-day stain panel was then stored at room temperature, and the 4-day stain panel placed in the stain oven at 80° C. for 4 days (96 hours).

Colorimetric readings were then taken on the 0- and 4-day stain panels using the procedure previously described after the 4-day stain panel had thoroughly cooled to room temperature. The 0-day stain panel colorimetric values were read twice and averaged, while the 4-day stain panel colorimetric values were read four times and averaged.

A white granule sample having a stain value as defined above of 5 or less is acceptable, with lower numbers preferred.

EXAMPLES

Example 1: Synthesis Tin-acrylate Monomer

A trialkyltin ester of methacrylic acid was synthesized essentially by the method of Montermoso (J. Polymer Science, Vol. 32, pages 523–525, 1958) as outlined in Scheme I below. Bis(tributyltin)oxide (51 grams, 0.09 mole; Aldrich Lot, #AZ04105JW) was combined with 150 ml of benzene (EM Science, Lot #31112135) in a 250 ml two-necked, round-bottomed flask equipped with a reflux condenser and a dropping funnel containing methacrylic acid (15 grams, 0.17 mole; Aldrich Lot, #TY03420PY). After the benzene solution had been cooled to approximately 20° C., the methacrylic acid was added dropwise in a manner so that the solution temperature remained below 30° C. Upon interaction of the reagents, a white, cloudy solution with droplets of water by-product had formed. After all of the acid had been added, the solution was heated under vacuum to 30° C. to remove the water of condensation. Approximately 20 ml of benzene was added to replace the benzene loss during evacuation. Once the water had been removed to give a solution which was completely clear, the remainder of the benzene was removed under vacuum. The pale liquid which remained was weighed to give 63.8 grams (98% conversion) of the trialkyltin ester.

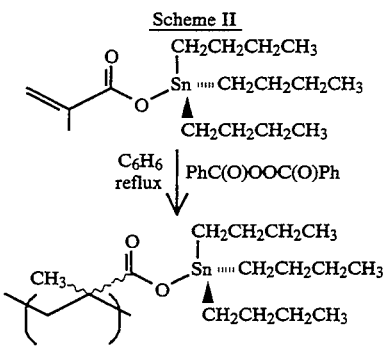

Examples 3–7 and Comparative Example A:
Preparation of a Tin Acrylate Polymer/Oil Coating on Shingles Various homogenous mixtures of the tin-acrylate polymer of Example 2 and slate oil (used as a carrier for the polymer) were applied as a topical coating on white granule-bearing three-tab asphalt shingles. The mixtures were prepared by melting the tin-acrylate polymer (see Table 1 for reagent amounts) at 140°–150° C. into a vial in air. Once the polymer melted, the appropriate amount of oil was added. The resulting homogenous,

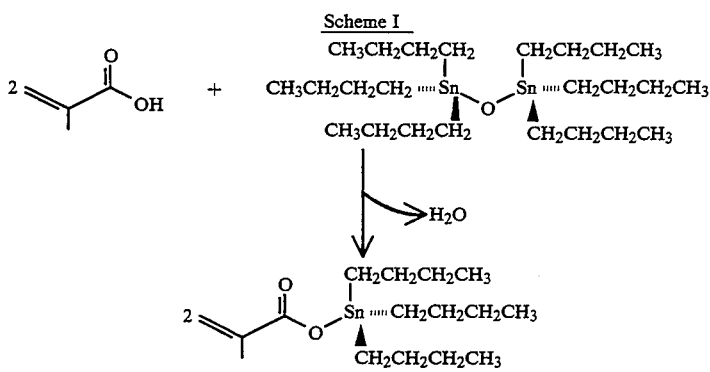

Example 2: Synthesis of Tin-acrylate Polymer.

A tin-acrylate polymer was also synthesized essentially by the method of Montermoso as outlined in Scheme II below. The tin acrylate ester synthesized above (30 grams, 0.12 mole) was dissolved in 50 ml of benzene and placed in a 100 ml round-bottomed flask equipped with a reflux condenser. To this solution was added 1 weight percent benzoyl peroxide (0.30 g; Aldrich, Lot #AZ06613KY) and the solution allowed to stand for 15 minutes at room temperature to initiate the reaction. The reaction mixture was heated at mild reflux for 3 hours after which time the benzene was removed by vacuum to give the desired polymer as a clear, pale yellow, rubbery solid in quantitative yield. The polymer was insoluble in benzene, water, water/$H_2SO_4$, and 1,1,1-trichloroethane.

Thermogravimetric Analysis (air, 35°–950° C.): 70.4% weight loss; ($N_2$, 35°–950° C.): 75.9% weight loss; Gel Permeation Chromatography (150° C., 1,2,4-trichlorobenzene carrier): $M_w$=10893, $M_n$=2129, Polydispersity=5.116.

mobile mixture was applied by brushing the polymer/oil mixture on one tab of a commercial three tab white asphalt shingle. The shingles were placed on an accelerated algae growth panel. Shingles were monitored every six months and rated 1–5, where 1 is no algae and 5 is complete algae infestation. After 6 months all shingles coated with the polymer/oil composition rated 1.

TABLE 1

| | Reagents for Topical Application of Tin-Acrylate Polymer in Oil | | |
|---|---|---|---|
| Tab | Amt Polymer (g) | Amt Oil (g) | Weight % Polymer |
| 3 | 1.42 | 12.76 | 10.01 |
| 4 | 3.28 | 9.83 | 25.01 |
| 5 | 4.30 | 4.33 | 49.83 |
| 6 | 5.22 | 1.75 | 74.89 |
| 7 | 0.09 | 8.94 | 0.997 |
| A | — | — | — |

Examples 8–10 and Comparative Examples B–D:
Tin-acrylate Polymer as a Post-treatment on White Kiln-fired Roofing Granules Six 1000 gram lots of kiln-fired white roofing granules (Wausau 93 single ceramic coating formulation)

which had not previously been treated with the standard silicone/oil post-treatment were heated at 180° C. for 1 hour. Each lot of hot granules was placed separately in a conventional paint shaker, quenched with 15 ml of tap water, and agitated for 30 seconds. Varying amounts and concentrations (Table 2) of the tin-acrylate polymer of Example 2 in slate oil were added and the granules were allowed to agitate for 5 additional minutes. The granules were then placed in a 80° C. oven for 1 hour to remove any residual water. Each lot was then tested for water repellency using a standard procedure. The procedure entails measuring the amount of time a drop of water takes to sink into a pile of roofing granules coated with the tin-acrylate/oil. A value of 50 seconds or more is considered acceptable. Results are presented in Table 2.

TABLE 2

Water Repellency of Various Weight Percentages of Tin-Acrylate Polymer in Oil

| Lot # | Amount of Polymer Solution (g) | Weight Percent Polymer % | Water Repellency (seconds) |
|---|---|---|---|
| B | 4.00 | 3.0 | 0 |
| C | 0.30 | 10 | 0 |
| D | 0.30 | 25 | 15 |
| 8 | 0.30 | 50 | 75 |
| 9 | 0.60 | 50 | 90 |
| 10 | 0.30 | >90 | 632 |

Example 11:

Tin-acrylate Polymer as a Binder for Roofing Granules

Raw uncoated base granules (100 grams, Little Rock 11-grade) were combined with $TiO_2$ (0.75 gram) and kaolin clay (1.33 gram) into a 500 ml beaker and mixed until the pigments were well dispersed onto the base granules surface. In a separate vial, distilled water (0.9 gram) and a fluorochemical surfactant (0.09 gram) were added together and mixed. In the same manner, the tin-acrylate monomer produced as in Example 1 (3 gram, $8.0 \times 10^{-3}$ mole) and benzoyl peroxide (0.03 gram, $1.24 \times 10^{-4}$ mole) were combined along with 1 ml of benzene. The two solutions were then added to the raw base granules mixture in small portions with stirring until all of the base granules had been uniformly coated. The coated base granules were then placed in a 80° C. oven for 1 hour to initiate the polymerization.

Alkalinity (5 minute) = 0.9 (acid); 21 hour = 0.90 (acid). Water Repellency >60 minutes. Reverse Wettability: 100-0. Colorimetric Data: $L^* = 62.49$, $a^* = -1.42$, $b^* = -1.89$. Adhesion Dry (based on average of two samples) = 0.50 gram; 1-Day Wet (based on average of two samples) = 0.85 gram; 7-Day Wet (based on average of three samples) = 1.09 gram.

Example 12:

Tin-acrylate/methacryloxypropyltrimethoxysilane Copolymer as a Binder for Roofing Granules Raw uncoated rock (100 grams, Little Rock 11-grade) was combined with $TiO_2$ (0.75 gram) and kaolin clay (1.33 gram) into a 500 ml beaker and mixed until the pigments were well dispersed onto the rock surface. In a separate vial, distilled water (0.9 gram) and fluorochemical surfactant (0.09 gram) were added together and mixed. In the same manner, the tin-acrylate monomer (1.5 gram, $4.0 \times 10^{-3}$ mole), methacryloxypropyltrimethoxysilane monomer (1.50 g, $6.03 \times 10^{-3}$ mole; Petrarch, Lot #110297), and benzoyl peroxide (0.03 gram, $1.24 \times 10^{-4}$ mole) were combined along with 1 ml of benzene. The two solutions were then added to the raw rock mixture in small portions with stirring until all of the rock had been uniformly coated. The coated material was then placed in a 80° C. oven for 2–3 hours to initiate the polymerization. The granules were removed from the oven, quenched with 2–3 ml of water, and returned to the oven to cure overnight. Alkalinity (5 minute) = 0.5 (acid); 15-minute = 0.40 (acid); 21 hour = 0.60 (acid). Water Repellency: >60 minutes. Reverse Wettability: 100-0. Colorimetric Data: $L^* = 64.21$, $a^* = -1.57$, $b^* = -2.11$. Stain: 0.23. Adhesion 7-Day Wet (based on average of seven samples) = 0.40 gram.

Various modifications and alterations of this invention will become apparent to those skilled in the art without departing from the scope of this invention, and it should be understood that this invention is not to be unduly limited to the illustrated embodiments set forth herein.

What is claimed is:

1. An algicidal granular material having an algicidal coating on base granules, the coating comprising an organic oil and a tin-acrylate polymer dispersed therein, the tin-acrylate polymer being derived from a monomer composition comprising free-radical polymerizable units independently selected from the group consisting of:

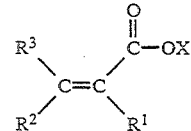

wherein:

X is selected from the group consisting of $SnR^4R^5R^6$ and hydrogen;

$R^1$–$R^3$ inclusive are the same or different and independently selected from the group consisting of hydrogen and organic radicals having from 1 to about 20 carbon atoms; and $R^4$–$R^6$ inclusive are the same or different and independently selected from the group consisting of hydrogen and alkyl groups having from 1 to about 7 carbon atoms;

with the provisos that $R^1$–$R^6$ inclusive are selected so that the polymer has a weight average molecular weight ranging from about 5,000 to about 50,000, and said polymer has an effective amount of said $SnR^4R^5R^6$ groups to render said granular material algicidal.

2. An algicidal granular material in accordance with claim 1 wherein said molecular weight ranges from about 5,000 to about 15,000.

3. An algicidal granular material in accordance with claim 1 wherein the tin-acrylate polymer is present at a weight percentage ranging from about 50 to about 90 as a percentage of a given weight of said oil and said polymer.

4. An algicidal granular material in accordance with claim 1 wherein all of said polymerizable units have $R^1$ = methyl, $R^2$ and $R^3$ = hydrogen, $X = SnR^4R^5R^6$, and $R^4$–$R^6$ inclusive = n-butyl.

5. An algicidal granular material in accordance with claim 1 wherein the polymer is a copolymer of two different polymerizable units.

6. An algicidal granular material in accordance with claim 1 wherein the polymer is a terpolymer of three different polymerizable units.

7. An algicidal granular material in accordance with claim 1 wherein said monomer composition comprises a siloxyl-acrylate monomer.

8. An algicidal composite sheet body suitable for use as a building material comprising a bituminous sheet material having a firmly adherent surfacing of granular material, at least some of the granular material comprising said algicidal granular material of claim 1.

9. An algicidal composite sheet body suitable for use as a building material comprising a bituminous sheet material having a firmly adherent surfacing of granular material, at least some of the granular material comprising said algicidal granular material of claim 4.

10. An algicidal composite sheet body suitable for use as a building material comprising a bituminous sheet material having a firmly adherent surfacing of granular material, at least some of the granular material comprising said algicidal granular material of claim 7.

11. A method of eliminating or controlling the growth of algae on a particulate matter-containing building material, the method comprising: including in said particulate matter-containing building material a granular material comprising said algicidal granular material of claim 1.

12. A method of eliminating or controlling the growth of algae on a particulate matter-containing building material, the method comprising: including in said particulate matter-containing building material a granular material comprising said algicidal granular material of claim 4.

13. A method of eliminating or controlling the growth of algae on a particulate matter-containing building material, the method comprising: including in said particulate matter-containing building material a granular material comprising said algicidal granular material of claim 7.

* * * * *